United States Patent [19]

Dickson

[11] Plant 4,222

[45] Mar. 14, 1978

[54] ROSE PLANT

[75] Inventor: Alexander Patrick Cuming Dickson, Newtownards, Northern Ireland

[73] Assignee: Jackson & Perkins Co., Medford, Oreg.

[21] Appl. No.: 756,082

[22] Filed: Jan. 3, 1977

[51] Int. Cl.[2] ..... A01H 5/00

[52] U.S. Cl. ..... Plt./20

[58] Field of Search ..... Plt./20–21

*Primary Examiner*—Robert E. Bagwill
*Attorney, Agent, or Firm*—Klarquist, Sparkman, Campbell, Leigh, Hall & Whinston

[57] ABSTRACT

A hybrid tea rose variety having bright red flowers opening from dark red buds, borne on an upright, heavily branched plant.

1 Drawing Figure

1

The present invention relates to a new and distinct cultivar of rose plant of the hybrid tea class which was originated by me by crossing Ernest H. Morse with Red Planet.

The primary objective of this breeding was to produce a vigorous, tall cultivar bearing large bright red blooms. This objective was substantially achieved along with other desirable improvements as evidenced by the following unique combination of characteristics which are outstanding in this new cultivar and which distinguish it from its parents as well as from all other cultivars of which I am aware:

1. An unusually upright habit, a vigorous plant, branching readily from the base.
2. Tight unopened buds of a deep red.
3. Opened buds to fully opened blooms a bright red, Wilson's Blood Red.
4. Strong heavy canes with less than average number of prickles.
5. Slight fragrance.
6. A better than average resistance to rose powdery mildew.
7. Large open flowers, often 6 or 7 inches in diameter.

Asexual reproduction of this new cultivar by budding as performed at Wasco, Calif., shows that the foregoing characteristics and distinctions come true to form and are established and transmitted through succeeding propagations.

The accompanying illustration show typical specimens of the vegetative growth and flowers of this new cultivar in different stages of development, depicted in color as nearly true as it is reasonably possible to make the same in a color illustration of this character.

The following is a detailed description of my new rose cultivar with color in terminology in accordance with Wilson's Horticultural Color Chart, except where ordinary dictionary significance of color is indicated.

Parentage:
*Seed parent.*—Ernest H. Morse.
*Pollen parent.*—Red Planet.
Classification:
*Botanical.*—Rosa hybrid.
*Commercial.*—Hybrid tea.

FLOWER

Observations made from specimens grown at Irvine, Calif., in July.

2

Blooming habit

Bud:
*Size.*—Approximately 1½ inches when petals start to unfurl.
*Form.*—Pointed ovoid.
*Color.*—When sepals first divid near Oxblood Red (00823), with occasional streaks near black where first exposed to light. When half blown; upper side of petals slightly darker than Blood Red (820); lower side of petals same color, with a less shiny surface.
*Sepals.*—Color: Outer surface Spinach Green (096-/3) partly covered with Garnet Brown (00918/3); inner surface lighter than Garnet Brown (00918/3) with white tomentum; three appendaged sepals lightly appendaged; two unappendaged sepals smooth edged.
*Receptacle.*—Color: Spinach Green (0960/3) and Garnet Brown (00918/3) where exposed to sun; Shape: narrow cone, very little enlargement; Size: small; Surface: smooth.
*Peduncle.*—Length: medium; Surface: very prickly; Color: Garnet Brown (00918/3); Strength: Stiff, heavy.
*Opening.*—Petal edges curl back slightly.

Bloom:
*Size.*—Large. Average open size 6 inches.
Borne.—Singly.
*Stems.*—Long, Normal.
*Form.*—When first open: high centered; Permanence: flattens.
*Petalage.*—Number of petals under normal conditions 20 to 25.
*Color.*—Center of flower: Upper side of petals slightly darker than Blood Red (820); reverse side of petals slightly darker than Blood Red (820); base of petals point of attachment slightly elongated, color is near Naples Yellow (403). General tonality from a distance Blood Red (820).
*Variegations.*—Darker streaks on outside petals between dividing sepals.
*Discoloration.*—General tonality at end of first day, no change; at end of third day, no change.
*Fragrance.*—Slight.

Petals:
*Texture.*—Thick.

*Shape.*—Round, base of petals at point of attachment slightly elongated.

*Form.*—Tips slightly recurved; edges slightly quilled.

*Arrangement.*—Loosely imbricated. Petaloids in center few.

*Persistence.*—Drop off cleanly.

*Lastingness.*—On the plant: Long; as cut flower: Long.

Reproductive parts:

*Stamens, anthers.*—Medium; color: yellow; Arrangement: regular around styles.

*Filaments.*—Color: Pink.

*Pollen.*—Gold Yellow.

*Styles.*—Color: Pink.

*Stigmas.*—Color: White.

PLANT

Form: Bush.

Growth: Vigorous, very upright. Plant habit is unusually vertical.

Foliage: Number of leaflets on normal mid-stem leaves, 5.

*Size.*—Large.

*Quantity.*—Normal.

*Color.*—New foliage: Garnet Brown (00918/3) Old foliage: Near Spinach Green (0960).

*Shape.*—Oval.

*Texture.*—Leathery.

*Edge.*—Serrated.

Serration.—Single, small.

*Petiole.*—Rachis—Color: Green. Underside: Large prickles. Upper side: Two rows of stipitate glands.

*Stipules.*—Long, serrated.

*Disease resistance.*—Resistant to mildew under normal growing conditions at Irvine, Calif.

Wood:

*New wood.*—Bronzy Brown. Bark: Smooth.

*Old wood.*—Green. Bark: Smooth.

Prickles:

*Quantity.*—On main stalks from base: few. On laterals from stalk: few.

*Form.*—Broad base, short, hooked downward.

*Color when young.*—Brown.

*Position.*—Irregular.

Small prickles:

*Quantity.*—On main stalks: few. On laterals: few. Color: Brown.

I claim:

1. A new and distinct cultivar of rose plant of the hybrid tea class, substantially as herein shown and described, characterized particularly as to novelty by the unique combination of its vigorous, unusually upright but heavily branched plant; dark red flower bud; bright red open flower of 20 to 25 petals; slight fragrance; strong heavy canes with few thorns and better than average resistance to rose powdery mildew.

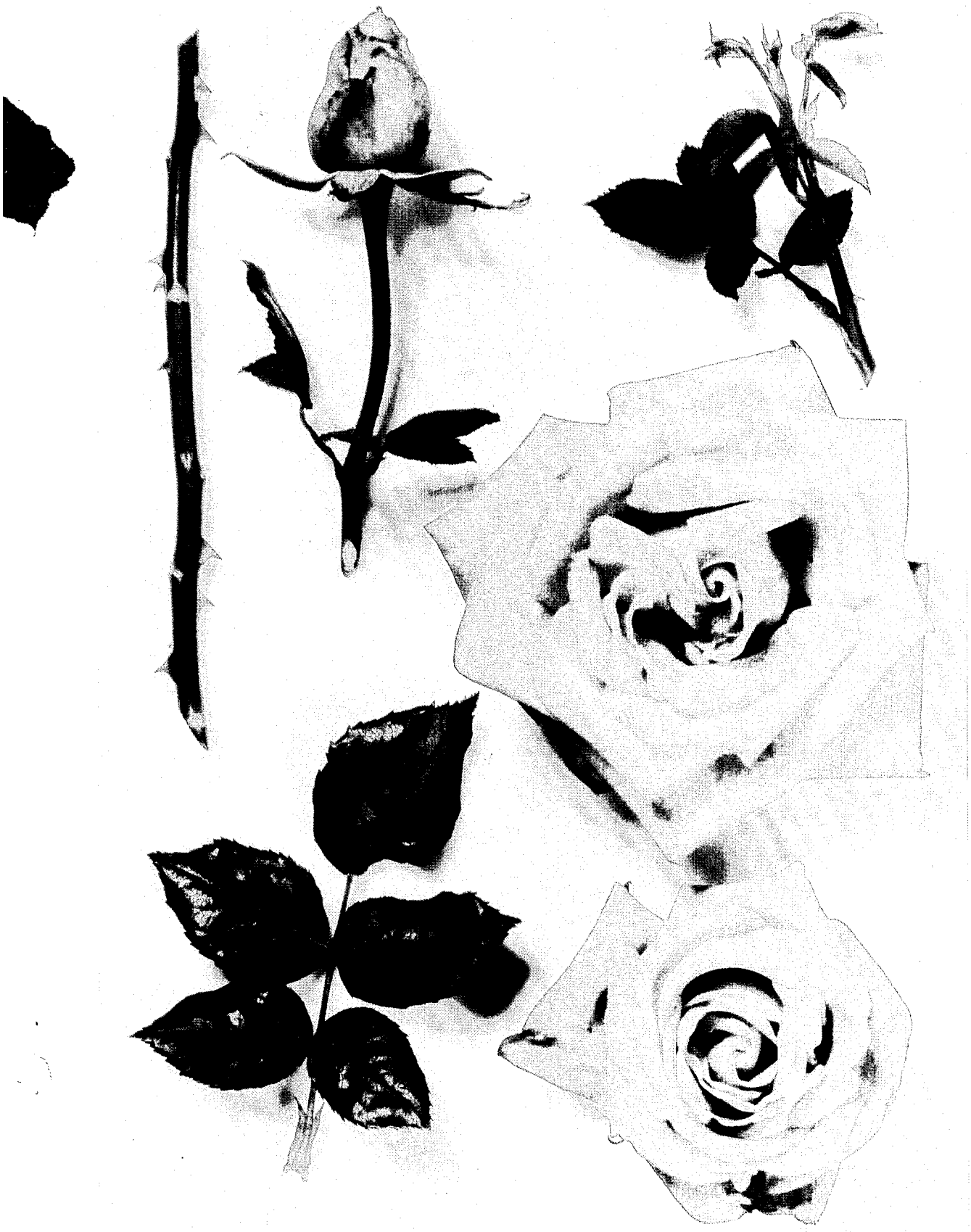

* * * * *